United States Patent
Diaz et al.

(10) Patent No.: US 6,426,431 B1
(45) Date of Patent: Jul. 30, 2002

(54) METHOD FOR INCREASING THE YIELD OF 2,6–NDA

(75) Inventors: Zaida Diaz; Thomas F. Brownscombe, both of Houston, TX (US)

(73) Assignee: Mossi & Ghisolfi Overseas S.A. (LU)

( * ) Notice: Subject to any disclaimer, the term of this patent is extended or adjusted under 35 U.S.C. 154(b) by 53 days.

(21) Appl. No.: 09/643,467

(22) Filed: Aug. 22, 2000

Related U.S. Application Data

(60) Provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,604, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, provisional application No. 60/151,578, filed on Aug. 30, 1999, and provisional application No. 60/151,489, filed on Aug. 30, 1999.

(51) Int. Cl.$^7$ ........................ C07L 51/42; C07L 51/347
(52) U.S. Cl. ...................................... 562/485; 562/481
(58) Field of Search ................... 562/485, 481

(56) References Cited

U.S. PATENT DOCUMENTS

| | | | | |
|---|---|---|---|---|
| 3,888,921 A | * | 6/1975 | Yamamoto et al. | |
| 4,130,719 A | * | 12/1978 | Cerfice et al. | |
| 4,709,088 A | * | 11/1987 | Hirose et al. | |
| 5,068,410 A | * | 11/1991 | Tananca et al. | |
| 5,481,033 A | * | 1/1996 | Alms et al. | |
| 5,728,870 A | * | 3/1998 | Holzhauer, et al. | |
| 5,770,764 A | * | 6/1998 | Zeitlin et al. | |
| 6,320,073 B1 | * | 11/2001 | June | |

FOREIGN PATENT DOCUMENTS

| | | | |
|---|---|---|---|
| JP | 000829 | * | 1/1974 |
| WO | 8805037 | * | 7/1988 |
| WO | 9312065 | * | 6/1993 |
| WO | 016074 | * | 3/2001 |
| WO | 1053246 | * | 7/2001 |

OTHER PUBLICATIONS

Shiyou Huagong (1997), 26(5) 325–331 Xia, Q.*

* cited by examiner

Primary Examiner—Paul J. Killos
(74) Attorney, Agent, or Firm—Renner, Kenner, Greive, Bobak, Taylor & Weber

(57) ABSTRACT

Disclosed is a method of increasing the yield of 2,6-NDA which comprises:

a) Dissolving a disproportionation reaction product containing a dialkali salt of 2,6-NDA in water and filtering off insoluble matter from the resulting solution;

b) Precipitating the monoalkali salt of 2,6-NDA (KHNDA) with $CO_2$;

c) Suspending said monoalkali salt in water in a weight ratio higher than 8:1, water: monosalt; and d) Heating at a temperature above 100° C. and at a pressure above 100 psig.

The improvements in yield are from about 20% to as high as 45%.

9 Claims, No Drawings

METHOD FOR INCREASING THE YIELD OF 2,6 –NDA

CROSS REFERENCE

This application is related to U.S. Application Ser. Nos. 60/151,489, 60/151,577, 60/151,607, 60/151,498, 60/151,602, 60/151,603, 60/151,529, 60/151,604, 60/151,606, 60/151,589, 60/151,497, 60/151,590, and 60/151,578, filed of even date Aug. 30, 1999.

FIELD OF THE INVENTION

This invention is related to the production of 2,6-naphthalene dicarboxylic acid (2,6-NDA). More particularly, this invention is related to a reaction step known in the art for the purification of 2,6-NDA in which the monosalt of 2,6-NDA, KHNDA, is heated in water or aqueous solvent to cause the disproportionation thereof, and to the stoichiometric limitation of the reaction to produce 50% 2,6-NDA on a molar basis. The present invention is a method for increasing the yield at least about 20% or more beyond the stoichiometric limitations.

BACKGROUND OF THE INVENTION

Aromatic dicarboxylic acids are highly useful organic compounds. They are often used as monomers for the preparation of polymeric materials. 2,6-naphthalene dicarboxylic acid is a particularly useful aromatic carboxylic acid, because it can be reacted with ethylene glycol to prepare poly(ethylene-2,6-naphthalate), PEN. Fibers and films manufactured from PEN display improved strength and superior thermal properties compared with other polyester materials such as polyethylene terephthalate. High strength fibers made from PEN can be used to make tire cords, and films made from PEN are advantageously used to manufacture magnetic recording tape and components for electronic applications.

It is known in the art to prepare aromatic dicarboxylic acids such as 2,6-NDA by primarily two methods. One is the liquid phase, metal catalyzed oxidation of an alkyl or acyl substituted aromatic compound. This method is described, for example, in U.S. Pat. Nos. 2,833,816; 3,856,855; 3,870,754; 4,933,491; and 4,950,786.

Alternatively, naphthalene monocarboxylic acid and naphthalene dicarboxylic acids other than 2,6-naphthalene dicarboxylic acid can be converted to 2,6-NDA, using a disproportionation reaction in the case of the monocarboxylic acids, or a rearrangement reaction in the case of other naphthalene dicarboxylic acids. Henkel and Cie first patented a reaction of naphthoic acid salts to 2,6 NDA. (See U.S. Pat. Nos. 2,823,231 and 2,849,482).

Currently most commercial processes use the oxidation method, though it requires expensive feedstock, forms oxidation products with impurities trapped within, and the product usually has to be submitted to esterification, so that the product is 2,6-naphthalene dicarboxylate, rather than 2,6-NDA. In view of the problems with the oxidation process and product, there has been much research on alternative routes to 2,6-NDA based on disproportionation. After a disproportionation or rearrangement reaction the dialkali metal salts have to be separated and directed through several steps in order to obtain the desired pure 2,6 -NDA. It is known to add mineral acid to free the 2,6-NDA. Neutralization of the disalt produced in the Henkel reaction is difficult without compromising the purity of the product 2,6-NDA. Other methods involve benzene extraction, evaporation, and sublimation. See for example U.S. Pat. Nos. 2,828,231, 2,849,482, 3,631,096.

Several references in the art have taught it is advantageous in the recovery of 2,6-NDA to precipitate the monoalkali salt of 2,6-NDA and disproportionate it to produce free 2,6-NDA. Precipitation of the monosalt with an acid such as $CO_2$, followed by disproportionation of the monosalt to make 2,6-NDA is a route that has the potential to result in high purity 2,6-NDA. Unfortunately this route only produces half a mole of 2,6-NDA from each mole of the 2,6 disalt present in the disproportionation product.

U.S. Pat. No. 3,671,578, to Teijin, discloses the monoalkali salt of 2,6-naphthalene dicarboxylic acid is disproportionated when heated in water or water-containing organic solvent, to form free dicarboxylic acid and by-product dialkali salt, and the former acid is precipitated.

This reference teaches the use of atmospheric pressure, or "slightly elevated" (Col. 3, line 68–70), and does not address the idea of increasing yield beyond stoichiometric limitations.

U.S. Pat. No. 3,888,921, to Teijin Ltd., discloses a method for purifying a dialkali salt of crude 2,6-naphthalene dicarboxylic acid comprising precipitating 40 to 97 mol percent of the dialkali 2,6-naphthalene dicarboxylate dissolved in an aqueous solution substantially as a monoalkali salt of the 2,6-naphthalenedicarboxylic acid while maintaining the pH of said aqueous solution at a value not lower than 6.3, and separating the precipitate, and converting the separated precipitate to a 2,6-naphthalene dicarboxylic acid by disproportionation.

Canadian Patent 864587 discloses a process for the preparation of 2,6-NDA which comprises heating a monoalkali salt of 2,6-NDA in water or water-containing organic solvent causing disproportionation thereof into 2,6-NDA and a dialkali salt and separating the 2,6-NDA by a method that includes dissolving a rearrangement reaction product containing dialkali salt of 2,6-naphthalene dicarboxylic acid in warm water, filtering off the insoluble matter therefrom, concentrating the remaining solution, whereby the filtrate is concentrated to such a degree that the precipitation yield of the dialkali salt precipitated when the concentrated liquid is cooled to room temperature reaches at least 70% and the purity of said precipitate exceeds 99% passing gaseous carbon dioxide through the aqueous solution of the precipitate recovered from the concentrated liquid, and recovering the resulting precipitate,and the mother liquour containing the side product dialkali salt of 2,6-naphthalene dicarboxylic acid is recycled into the carbon dioxide reaction step. This reference teaches at page 7, line 12, "Atmospheric pressure is employable, but the reaction can be . . . at elevated pressures and temperatures above 100° C.". This reference does not address the possibility of increased yields.

U.S. Pat. No. 5,175,354 discloses a process for preparing 2,6-NDA by reacting at least one of 2,6-NDA dipotassium salt and 2,6-NDA monopotassium salt with a benzenecarboxylic acid to yield solid 2,6-NDA and an aqueous solution of a benzenecarboxylic acid potassium salt, separating the solid 2,6-NDA from the aqueous solution, recovering the benzenecarboxylic acid potassium salt from the aqueous solution, reacting the benzenecarboxylic acid potassium salt with naphthalene to yield 2,6-NDA dipotassium salt, and recycling the 2,6-NDA dipotassium salt.

Although the step of heating the monopotassium salt of 2,6-NDA in water or aqueous solvent to disproportionate it to produce 2,6-NDA has been disclosed in the art, a disadvantage is that the maximum yield of 2,6-NDA has appeared to be limited by stoichiometry to 50% on a molar basis. None of the references found address the concept of increasing yields well beyond the stoichiometric limitations. It would be a distinct advance in the art if it were possible to substantially improve the yield of 2,6-NDA. This would be extremely valuable economically in any integrated process for producing 2,6-NDA.

SUMMARY

In accordance with the foregoing the present invention is a method of substantially increasing the yield of 2,6-NDA which comprises:

a) Dissolving the disproportionation reaction product of potassium naphthoate, containing the dialkali salt of 2,6-NDA(K2NDA) in water to form an aqueous solution and filtering off insoluble matter from the resulting solution;

b) Reacting said aqueous K2NDA solution at a $CO_2$ pressure of about 0–200 psig and a temperature of about 0–50° C. to selectively precipitate the monopotassium salt of 2,6-NDA (KHNDA);

c) Suspending said monopotassium salt in water in a weight ratio higher than 8:1, water: monosalt; and d) Heating said monopotassium salt in water at a temperature above 100° C. and at a $CO_2$ pressure above 100 psig causing disproportionation to form 2,6-NDA and K2NDA.

The present invention provides a method of increasing the yields from the stoichiometric limitation of 50% to as high as 72%.

DETAILED DESCRIPTION OF THE INVENTION

In the present invention we have discovered that there are critical conditions for the disproportionation of KHNDA to 2,6-NDA which substantially increase the molar yield. The predicted 50% is calculated by assuming the only reaction is disproportionation. The increased yield in the present invention is believed to be due to direct neutralization of some of the KHNDA with $CO_2$. This is very unexpected given the relative magnitude of the pKa's. The increase may also be due in part to neutralization of the K2NDA product to KHNDA, where the KHNDA can continue to disproportionate.

The starting materials for the present invention are the dipotassium salts of 2,6-NDA and 2,3-NDA, K2NDA. It is possible the dipotassium salts could be the product of oxidation, as described in U.S. Pat. No. 3,888,921, but in the present invention, it is contemplated the dipotassium salts of NDA will be the product of the disproportionation of potassium naphthoate in the presence of a ZnO catalyst, as discussed in copending U.S. Application Serial No. 60/151, 577, incorporated by reference herein in its entirety. Following the disproportionation reaction in copending Serial No. 60/151,577, the product is washed with water and the catalyst is removed. The disalt of 2,6-NDA, K2NDA, is selectively precipitated and purified. It can optionally be treated with a solid adsorbing agent to remove impurities.

The next step in the recovery of 2,6-NDA is the precipitation of the monosalt of 2,6-NDA with carbon dioxide. The precipitation produces potassium bicarbonate, 2,3-KHNDA, and the solid mono-potassium salt of 2,6-NDA, 2,6 - KHNDA. Of most concern in this step is the recovery of 2,6-KHNDA as the solid mono-salt and the rejection of 2,3-KHNDA from the crystals.

The monopotassium salt of 2,6-NDA (KHNDA) is selectively precipitated from an aqueous K2NDA solution (about 20%) at 0–200 psi $CO_2$ pressure, and 0–50° C., for about 30 minutes. The fact that the precipitation can be done effectively at modest pressure allows centrifugation of the product without releasing pressure. The centrate also contains dissolved potassium bicarbonate and 2,3-KHNDA.

The next step is the focus of the present invention. The KHNDA solids are disproportionated in a reaction that can be represented by the following:

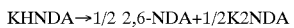

$$\text{KHNDA} \rightarrow 1/2\ 2,6\text{-NDA} + 1/2\text{K2NDA} \qquad \text{Eq. 1}$$

Though it would be extremely advantageous and commercially desirable to substantially increase the yield of this reaction, heretofore believed to be limited by stoichiometry, the subject does not appear to have been addressed in the art. We have discovered critical conditions which increase the yield from 50% to at least about 60%, and as high as 72%, while maintaining high product purity, as shown by the low potassium levels achieved. See Examples 1–9.

In the present invention KHNDA solids are diluted with water in a ratio of water to solids higher than 8:1 and reacted for less than an hour, preferably about 20 to 30 minutes at 150° C., under at least 100 psig $CO_2$ pressure. What is expected according to what is known in the art is that in this reaction step, two moles of the monopotassium salt of 2,6 NDA (KHNDA) will disproportionate to form one mole each of 2,6 NDA(s), and K2NDA with a maximum yield of about 50%, however we have found, at the conditions noted, the measured molar yield is 60–72%.

The weight ratio of water to salt in the disproportionation step is important. A suitable ratio is 9–25:1. The ratio employed in Examples 1–9 was 5–20:1, and the preferred ratio is about 10–20:1. It was observed that at water to salt ratios below 10:1 the purity of 2,6-NDA decreased, possibly due to coprecipitation of the monosalt.

The contact time should be about 15 minutes to 1 hour. The contact time used in the examples was 30 minutes, however, from what has been observed in other work, 15 minutes should be sufficient.

By carrying out the reaction in the presence of $CO_2$ at elevated pressures, the yield of 2,6-NDA is increased greatly. The increase in yield in the present invention requires that the $CO_2$ pressure be well above atmospheric. $CO_2$ pressure should at least be greater than 100 psig. Suitable pressure is from about 100 to 1000 psig $CO_2$. The examples demonstrate pressures of 200 psig and 700 psig. Probably the most desirable overall results were obtained using a pressure of about 200 psig $CO_2$. The greatly increased yields may be due to neutralization of KHNDA by $CO_2$, which is unexpected given the relative magnitudes of the pKa's. 2,6-NDA (pKa=3.3) is a stronger acid than CO2 (pKa=6.4) and on this basis KHNDA would not be expected to accept a proton from CO2. The increased yields may also be due in part to neutralization of the K2NDA product to KHNDA which can then continue to disproportionate according to Equation 1.

The reactor effluent from the disproportionation of the monopotassium salt of 2,6-NDA is filtered to give a 2,6-NDA solid, and a filtrate containing predominantly 2,6 K2NDA and $KHCO_3$. The solid cake is rinsed with water.

The following examples will serve to illustrate specific embodiments of the invention disclosed herein. These examples are intended only as a means of illustration and should not be construed as limiting the scope of the invention in any way. Those skilled in the art will recognize variations that may be made without departing from the spirit of the disclosed invention.

In the examples, the solid products were analyzed for 2,6-NDA by liquid chromatography and for potassium by ion chromatography. The molar yields of 2,6-NDA were calculated from the number of millimoles of 2,6-KHNDA initially suspended in solution, and the number of millimoles of 2,6-NDA precipitated upon disproportionation.

EXAMPLE 1

In Example 1, 7 g of 2,6-KHNDA obtained from 2,6-K2NDA by precipitation with $CO_2$ was suspended in water in a weight ratio of 20:1, water to monosalt. The wt % of 2,6-NDA in the starting solids, expressed as the acid of molecular weight 216, was 79.7%, so the starting material contained 25.8 mmoles of 2,6-KHNDA. The monosalt was placed in an autoclave and heated at about 150° C. with 200 psig $CO_2$ for 30 minutes At the end of the experiment, the autoclave contents were filtered and the solids were analyzed to determine the 2,6-NDA and potassium content. From this, the yield of 2,6-NDA was calculated. It was determined the precipitate weight was 4.06 grams. The wt % of 2,6-NDA in the precipitate, expressed as the acid, was 92.5%, which corresponds to 17.4 mmoles. The level of potassium in the precipitate was 425 ppm. The %molar 2,6-NDA yield was calculated to be 67%, since 25.8 mmoles of 2,6-KHNDA produced 17.4 mmoles of 2,6-NDA.

EXAMPLE 2

In Example 2, 7.6 g of 2,6-KHNDA obtained from 2,6-K2NDA by precipitation with $CO_2$ was suspended in water in a weight ratio of 10:1, water to monosalt. The wt % of 2,6-NDA in the starting solids was 79.7%, so the starting material contained 28.0 mmoles of 2,6-KHNDA. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 4.64 grams. The wt % of 2,6-NDA in the precipitate was 92.4%, which corresponds to 19.8 mmoles. The level of potassium in the precipitate was 1390 ppm. The %molar 2,6-NDA yield was calculated to be 71%, based on obtaining 19.8 mmoles from the initial 28.0 mmoles.

EXAMPLE 3

In Example 3, 8.5 g of 2,6-KHNDA obtained from 2,6-K2NDA by precipitation with $CO_2$ was suspended in water in a ratio of 20:1, water to monosalt. The wt % of 2,6-NDA in the starting solids was 79.3%, corresponding to 31.2 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 5.05 grams. The wt % of 2,6-NDA in the precipitate was 92.8%, which corresponds to 21.7 mmoles. The potassium level in the precipitate was 370 ppm. The %molar 2,6-NDA yield was calculated to be 70%.

EXAMPLE 4

In Example 4, 8.5 g of 2,6-KHNDA obtained from 2,6-K2NDA by precipitation with $CO_2$ was suspended in water in a weight ratio of 10:1, water to monosalt. The wt % of 2,6-NDA in the starting solids was 79.3%, which corresponds to 31.2 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 4.93 grams. The wt % of 2,6-NDA in the precipitate was 91.9%, corresponding to 21.0 mmoles, and the level of potassium in the precipitate was 480 ppm. The %molar 2,6-NDA yield was calculated to be 67%.

EXAMPLE 5

In Example 5, 5 g of 2,6-KHNDA obtained from 2,6-K2NDA by precipitation with $CO_2$ was suspended in water in a ratio of 20:1, water to monosalt. The wt % of 2,6-NDA in the starting solids was 79.6%, corresponding to 18.4 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 3.13 grams. The wt % of 2,6-NDA in the precipitate was 91.1%, corresponding to 13.2 mmoles. The level of potassium in the precipitate was 386 ppm. The %molar 2,6-NDA yield was calculated to be 72%.

EXAMPLE 6

In Example 6, 5 g of 2,6-KHNDA obtained from 2,6-K2NDA by precipitation with $CO_2$ was suspended in water in a ratio of 10:1, water to monosalt. The wt % of 2,6-NDA in the starting solids was 79.6%, which corresponds to 18.4 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 2.86 grams. The wt % of 2,6-NDA in the precipitate was 90.0%, corresponding to 11.9 mmoles, and the level of potassium in the precipitate was 545 ppm. The %molar 2,6-NDA yield was calculated to be 65%.

EXAMPLE 7

In Example 7, 6.6 g of 2,6-KHNDA obtained from 2,6-K2NDA by precipitation with $CO_2$ was suspended in water in a ratio of 5:1, water to monosalt. The wt % of 2,6-NDA in the starting solids was 80.0%, corresponding to 24.4 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 5.0 grams. The wt % of 2,6-NDA in the precipitate was 85.0%, corresponding to 19.7 mmoles, and the level of potassium in the precipitate was 99000 ppm. The %molar 2,6-NDA yield was calculated to be 80.0%. The purity of the 2,6-NDA, as evidenced by the potassium level, was lower than in Examples 1–6. This is due to the lower water to monosalt weight ratio used in this Example (5:1).

EXAMPLE 8

In Example 8, 5.7 g of 2,6-KHNDA obtained from 2,6-K2NDA by precipitation with $CO_2$ was suspended in water in a ratio of 8:1, water to monosalt. The wt % of 2,6-NDA in the starting solids was 79.5%, corresponding to 21.0 mmoles. The monosalt was placed in an autoclave and heated at about 150° C. with 200 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 3.9 grams. The wt % of 2,6-NDA in the precipitate was 87.4%, corresponding to 15.8 mmoles, and the level of potassium in the precipitate was 50000 ppm. The %molar 2,6-NDA yield was calculated to be 75.0%. The purity of the 2,6-NDA, based on the potassium level, was lower than in Examples 1–6. This is due to the relatively low water to monosalt weight ratio used in this Example (8:1).

EXAMPLE 9

In Example 9, 6 g of 2,6-KHNDA obtained from 2,6-K2NDA by precipitation with $CO_2$ was suspended in water in a ratio of 20:1, water to monosalt. The wt % of 2,6-NDA in the starting solids was 75.7%, corresponding to 21.0 mmoles. The monosalt was placed in an autoclave and heated at about 150° C. with 700 psig $CO_2$ for 30 minutes. At the end of the experiment, the autoclave contents were filtered and the solids were analyzed to determine the 2,6-NDA and potassium content. From this, the yield of 2,6-NDA was calculated. It was determined the precipitate weight was 3.48 grams. The wt % of 2,6-NDA in the precipitate was 92.6%, which corresponds to 14.9 mmoles, and the level of potassium in the precipitate was 170 ppm. The %molar 2,6-NDA yield was calculated to be 71.0%.

COMPARATIVE EXAMPLES 10–12

In Comparative Examples 10–12, a procedure identical to that used in Examples 1–9 was followed except no $CO_2$ pressure was applied. The temperature in all cases was 150° C. and the reaction time was again 30 minutes. The results are given in Table 1:

TABLE 1

|  | Example 10 | Example 11 | Example 12 |
| --- | --- | --- | --- |
| Starting solids (g) | 3 | 5 | 6 |
| 2,6-NDA in starting solids (wt %) | 80.1 | 80.1 | 81.5 |
| Water/monosalt ratio | 20 | 10 | 20 |
| Precipitate weight (g) | 1.41 | 2.41 | 2.69 |
| 2,6-NDA in precipitate (wt %) | 92.3 | 91.2 | 92.7 |
| K in precipitate (ppm) | 540 | 24000 | 120 |
| 2,6-NDA yield (% molar) | 54 | 55 | 51 |

Examples 10–12 show lower molar yields of 2,6-NDA than Examples 1–9. These lower yields are due to the absence of $CO_2$ in Examples 10–12. Also, comparison of Example 11 with Examples 2, 4 and 6 shows that at the same water to monosalt ratio (10:1) the purity of the 2,6-NDA produced is higher in the presence of $CO_2$ than in the absence of $CO_2$.

We claim:

1. A method of increasing the yield of 2,6-NDA which comprises:
    a) Dissolving the disproportionation reaction product of potassium naphthoate, comprising the dialkali salt of 2,6-NDA(K2NDA), in water to form an aqueous solution and filtering off insoluble matter from the resulting solution;
    b) Reacting said aqueous K2NDA solution at a $CO_2$ pressure of about 0–200 psig and a temperature of about 0–50° C. to selectively precipitate the monopotassium salt of 2,6-NDA (KHNDA);
    c) Suspending said monopotassium salt in water in a weight ratio higher than 8:1, water: monosalt; and
    d) Heating said monopotassium salt in water at a temperature above 100° C. and at a $CO_2$ pressure above 100 psig causing disproportionation to form 2,6-NDA and K2NDA.

2. The method of claim 1 wherein the monopotassium salt of 2,6-NDA (KHNDA) is suspended in water in a weight ratio of greater than 10:1, water to monosalt to about 20:1 water: monosalt.

3. The method of claim 1 wherein the monopotassium salt of 2,6-NDA(KHNDA) is suspended in water in a weight ratio higher than 8:1 water: monosalt.

4. The method of claim 1 wherein the monoalkali salt in water is heated at a temperature of from about 120–170° C.

5. The method of claim 4 wherein the monoalkali salt in water is heated at a temperature of from about a 140–160° C.

6. The method of claim 1 wherein the monoalkali salt in water is heated at a $CO_2$ pressure of about 150 to 800 psig.

7. The method of claim 6 wherein the monoalkali salt in water is heated at a $CO_2$ pressure of about 175–250 psig.

8. In a process for the recovery of pure 2,6-NDA from the dipotassium salt of 2,6-NDA formed by the disproportionation of potassium naphthoate by:
    a) Dissolving the dipotassium salt of 2,6-NDA in water and filtering off insoluble matter from the resulting solution;
    b) Selectively precipitating the monopotassium salt of 2,6-NDA (KHNDA) from an aqueous K2NDA solution at a $CO_2$ pressure of about 0–200 psig and a temperature of about 0–50° C.; and
    c) Disproportionating the monopotassium salt to produce 2,6-NDA, the improvement which provides an improvement in yield of 20% or more which comprises:
    d) Suspending said monopotassium salt in water in a weight ratio of 10–20:1, water: monosalt; and
    e) Heating said monopotassium salt in water at a temperature of about 140–160° C. and at a $CO_2$ pressure of about 175 to 800 psig to disproportionate the monopotassium salt (KHNDA) to 2,6-NDA and K2NDA.

9. The method of claim 8 wherein the $CO_2$ pressure is from about 175–250 psig.

* * * * *